(12) United States Patent
Hashimoto et al.

(10) Patent No.: US 8,399,835 B2
(45) Date of Patent: Mar. 19, 2013

(54) LIGHT MEASUREMENT APPARATUS AND A TRIGGER SIGNAL GENERATOR

(75) Inventors: Masaichi Hashimoto, Miyagi (JP); Akiyoshi Irisawa, Miyagi (JP)

(73) Assignee: Advantest Corporation, Tokyo (JP)

( * ) Notice: Subject to any disclaimer, the term of this patent is extended or adjusted under 35 U.S.C. 154(b) by 930 days.

(21) Appl. No.: 12/487,876

(22) Filed: Jun. 19, 2009

(65) Prior Publication Data

US 2010/0294934 A1 Nov. 25, 2010

(30) Foreign Application Priority Data

May 25, 2009 (JP) ................................. 2009-125570

(51) Int. Cl.
*G01J 3/433* (2006.01)
(52) U.S. Cl. .................................. 250/336.1; 250/341.2
(58) Field of Classification Search ................ 250/341.2
See application file for complete search history.

(56) References Cited

U.S. PATENT DOCUMENTS

| | | | |
|---|---|---|---|
| 5,585,913 A | 12/1996 | Hariharan et al. | |
| 5,778,016 A | 7/1998 | Sucha et al. | |
| 6,271,921 B1 * | 8/2001 | Maris et al. ................... | 356/432 |
| 6,396,856 B1 | 5/2002 | Sucha et al. | |
| 6,549,290 B2 * | 4/2003 | Miura et al. ................... | 356/614 |
| 6,970,287 B1 * | 11/2005 | Watkins et al. ............... | 359/368 |
| 7,214,940 B2 * | 5/2007 | Cluff et al. ................. | 250/341.1 |
| 7,307,258 B2 * | 12/2007 | Tao et al. .................... | 250/341.1 |
| 7,580,432 B2 | 8/2009 | Sucha et al. | |
| 2002/0097761 A1 | 7/2002 | Sucha et al. | |
| 2005/0117830 A1 * | 6/2005 | Hartog et al. .................... | 385/12 |
| 2006/0285850 A1 * | 12/2006 | Colpitts et al. ................ | 398/108 |
| 2008/0158565 A1 * | 7/2008 | Opsal et al. ................... | 356/445 |
| 2008/0165355 A1 | 7/2008 | Yasui et al. | |
| 2009/0296749 A1 | 12/2009 | Sucha et al. | |

FOREIGN PATENT DOCUMENTS

| | | |
|---|---|---|
| JP | 10-096610 | 4/1998 |
| WO | 2006/092874 | 9/2006 |

OTHER PUBLICATIONS

Bartels et al., "Ultrafast time-domain spectroscopy based on high-speed asynchronous optical sampling", Rev. Sci, Instrum., vol. 78, pp. 035107 (2007).
Yasui et al., "Asynchronous optical sampling terahertz time-domain spectroscopy for ultrahigh spectral resolution and rapid data acquisition", Appl. Phys. Lett., vol. 87, pp. 061101 (2005).
Bartels et al., "High-resolution THz spectrometer with kHz scan rates", Optics express, vol. 14, pp. 403 (2006).

(Continued)

*Primary Examiner* — David Porta
*Assistant Examiner* — Djura Malevic
(74) *Attorney, Agent, or Firm* — Greenblum & Bernstein, P.L.C.

(57) ABSTRACT

A trigger signal generation device restrains a jitter from being generated in a measurement result of light, such as terahertz light, that has transmitted through a device under test. The device includes a first photoelectric conversion unit that applies photoelectric conversion to a probe light pulse, a second photoelectric conversion unit that applies photoelectric conversion to a pump light pulse, a first amplification unit that amplifies an output from the first photoelectric conversion unit, and a second amplification unit that amplifies an output from the second photoelectric conversion unit. The device also includes a trigger signal output unit that outputs a cross-correlation of outputs of the first amplification unit and the second amplification unit as a trigger signal, and a period difference adjustment unit that adjusts a difference in periods.

27 Claims, 8 Drawing Sheets

OTHER PUBLICATIONS

Bartels et al., "Femtosecond time-resolved optical pump-probe spectroscopy at kilohertz-scan-rates iver nanosecond-time-delays without mechanical delay line", Appl. Phys. Lett., vol. 88, pp. 041117 (20066).

Janke et al,, Asynchronous optical sampling for high-speed characterization of integrated resonant terahertz sensors, Optics Letters, vol. 30, pp. 1405 (2005).

Takagi et al., "Subpicosecond optical sampling spectrometer using asynchronous tunable mode-locked lasers", Rev. Sci. Instrum., vol. 70, pp. 2218 (1999).

The Institute of Electronics, Information and Communication Engineers, Technical Report of IEICE OCS98-53 (Oct. 1998), pp. 19-24.

Bartels et al., "High-resolution THz spectrometer with kHz scan rates", Optics express, vol. 14, pp. 430-437 (Jan. 9, 2006).

Takagi et al., "Subpicosecond optical sampling spectrometer using asynchronous tunable mode-locked lasers", Review of Scientific Instruments, vol. 70, No. 5, pp. 2218-2224 (May 1999).

G. Zhu et al., "80Gb/s clock recovery with phase locked loop based on LiNbO3 modulators", Optics Express, vol. 12, No. 15, Jul. 26, 2004, pp. 3488-3492.

* cited by examiner

LIGHT MEASUREMENT APPARATUS AND A TRIGGER SIGNAL GENERATOR

BACKGROUND ART

1. Field of the Invention

The present invention relates to measurement of light.

2. Description of the Prior Art

There has been conventionally known a method for measuring a device under test (DUT) by a terahertz detector receiving terahertz light A (in a form of pulse) which has been fed from a terahertz emitter to the DUT, and has transmitted through the DUT, and light B having the pulse period which is slightly different from the pulse period of terahertz light A (refer to ABSTRACT of Patent Document 1, for example).

According to the above-described conventional technology, a detection result by the terahertz detector, and a trigger signal indicating an origin of time are fed to a digital oscilloscope to measure the DUT. It should be noted that the trigger signal is generated by obtaining sum frequency generation (SFG) cross-correlation of a part of an optical pulse (a probe light fed to the terahertz detector) output from a first femtosecond laser and a part of an optical pulse (a pump light fed to the terahertz emitter) output from a second femtosecond laser (refer to FIG. 20 of Patent Document 1, for example).

It should be noted that the trigger signal is also described in Non-Patent Documents 1 to 7.

(Patent Document 1) WO 2006/092874, Pamphlet
(Non-Patent Document 1) Bartels et al, "Ultrafast time-domain spectroscopy based on high-speed asynchronous optical sampling", Rev. Sci. Instrum., vol. 78, pp. 035107 (2007)
(Non-Patent Document 2) T. Yasui et al, "Asynchronous optical sampling terahertz time-domain spectroscopy for ultrahigh spectral resolution and rapid data acquisition", Appl. Phys. Lett., vol. 87, pp. 061101 (2005)
(Non-Patent Document 3) A. Bartels et al, "High-resolution THz spectrometer with kHz scan rates", Optics express, vol. 14, pp. 430 (2006)
(Non-Patent Document 4) A. Bartels et al, "Femtosecond time-resolved optical pump-probe spectroscopy at kilohertz-scan-rates over nanosecond-time-delays without mechanical delay line", Appl. Phys. Lett., vol. 88, pp. 041117 (2006)
(Non-Patent Document 5) C. Janke et al, "Asynchronous optical sampling for high-speed characterization of integrated resonant terahertz sensors", Optics Letters, vol. 30, pp. 1405 (2005)
(Non-Patent Document 6) Y. Takagi et al, "Subpicosecond optical sampling spectrometer using asynchronous tunable mode-locked lasers", Rev. Sci. Instrum., vol. 70, pp. 2218 (1999)
(Non-Patent Document 7) IEICE Technical Report, OCS98-53

SUMMARY OF THE INVENTION

However, when the SFG cross-correlation of the part of the probe light and the part of the pump light is obtained, the power of the probe light fed to the terahertz detector decreases. The power of the pump light fed to the terahertz emitter also decreases.

It should be noted that, when the power of the part of the probe light and the power of the part of the pump light subject to the cross-correlation are reduced, the probe light fed to the terahertz detector and the pump light fed to the terahertz emitter can be increased. However, detection of cross-correlation light becomes difficult in this case.

On this occasion, it is also conceivable to apply photoelectric conversion to the part of the probe light and the part of the pump light, to amplify them up to predetermined powers, and to mix them by a mixer, thereby obtaining the trigger signal.

However, if the trigger signal is obtained by means of the mixing by the mixer, a jitter generated in the terahertz light which has transmitted through the DUT and a jitter generated in the trigger signal are different from each other. Thus, a jitter is generated in a measurement result of the terahertz light which has transmitted through the DUT.

It is therefore an object of the present invention to restrain a jitter from being generated in a measurement result of light such as terahertz light which has transmitted through a DUT.

According to the present invention, a first optical measurement device includes: a detected light pulse output unit that receives a pump light pulse from a pump light source, and outputs detected light pulse having the same repetition frequency as the repetition frequency of the pump light pulse; a signal output device that receives the detected light pulse and a probe light pulse from a probe light source, and outputs a signal corresponding to a power of the detected light pulse upon the reception of the probe light pulse; a waveform measurement unit that measures a waveform of the output from the signal output device by detecting the output from the signal output device for a period from reception of a trigger signal to reception of a next trigger signal; a first photoelectric conversion unit that applies photoelectric conversion to the probe light pulse; a second photoelectric conversion unit that applies photoelectric conversion to the pump light pulse; a first amplification unit that amplifies an output from the first photoelectric conversion unit; a second amplification unit that amplifies an output from the second photoelectric conversion unit; a trigger signal output unit that outputs a cross-correlation of outputs of the first amplification unit and the second amplification unit as the trigger signal; and a period difference adjustment unit that adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed, as the output from the second amplification unit, to the trigger signal output unit, wherein the repetition frequency of the detected light pulse and the repetition frequency of the probe light pulse are different from each other.

According to the thus constructed first optical measurement device, a detected light pulse output unit receives a pump light pulse from a pump light source, and outputs detected light pulse having the same repetition frequency as the repetition frequency of the pump light pulse. A signal output device receives the detected light pulse and a probe light pulse from a probe light source, and outputs a signal corresponding to a power of the detected light pulse upon the reception of the probe light pulse. A waveform measurement unit measures a waveform of the output from the signal output device by detecting the output from the signal output device for a period from reception of a trigger signal to reception of a next trigger signal. A first photoelectric conversion unit applies photoelectric conversion to the probe light pulse. A second photoelectric conversion unit applies photoelectric conversion to the pump light pulse. A first amplification unit amplifies an output from the first photoelectric conversion unit. A second amplification unit amplifies an output from the second photoelectric conversion unit. A trigger signal output unit outputs a cross-correlation of outputs of the first amplification unit and the second amplification unit as the trigger signal. A period difference adjustment unit adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed, as the output from the second amplification unit, to the trigger signal output unit. Furthermore, the repetition frequency of the detected light pulse and the repetition frequency of the probe light pulse are different from each other.

According to the first optical measurement device of the present invention, the trigger signal output unit may include: an electric modulation unit that modulates the output from the first amplification unit according to the output from the second amplification unit; an amplification unit that amplifies an output from the electric modulation unit; and a detection unit that detects an output from the amplification unit according to the envelope detection.

According to the first optical measurement device of the present invention, a period from the output of the probe light pulse from the probe light source until the probe light pulse is fed to the signal output device is T1; a period from the output of the pump light pulse from the pump light source until the detected light pulse generated from the output pump light pulse is fed to the signal output device is T2; and the period difference adjustment unit may adjust the period difference so that a value obtained by subtracting the period T3 from the period T4 is equal to a value obtained by subtracting the period T1 from the period T2.

According to the first optical measurement device of the present invention, the period difference adjustment unit may make such an adjustment that the period T4 is equal to the period T2, and the period T3 is equal to the period T1.

According to the first optical measurement device of the present invention, the period difference adjustment unit may cause the periods T4, T2, T3 and T1 are equal to each other.

According to the first optical measurement device of the present invention, the pump light source and the detected light pulse output unit may be connected with each other via an optical fiber; the probe light source and the signal output device may be connected with each other via an optical fiber; the probe light source and the first photoelectric conversion unit may be connected with each other via an optical fiber; and the pump light source and the second photoelectric conversion unit may be connected with each other via an optical fiber.

According to the present invention, a second optical measurement device includes: a detected light pulse output unit that receives a pump light pulse from a pump light source, and outputs detected light pulse having the same repetition frequency as the repetition frequency of the pump light pulse; a signal output device that receives the detected light pulse and a probe light pulse from a probe light source, and outputs a signal corresponding to a power of the detected light pulse upon the reception of the probe light pulse; a waveform measurement unit that measures a waveform of the output from the signal output device by detecting the output from the signal output device for a period from reception of a trigger signal to reception of a next trigger signal; a first photoelectric conversion unit that applies photoelectric conversion to the probe light pulse; a first amplification unit that amplifies an output from the first photoelectric conversion unit; a trigger signal output unit that outputs a cross-correlation of the output of the first amplification unit and the pump light pulse as the trigger signal; and a period difference adjustment unit that adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed to the trigger signal output unit, wherein the repetition frequency of the detected light pulse and the repetition frequency of the probe light pulse are different from each other.

According to the thus constructed second optical measurement device, a detected light pulse output unit receives a pump light pulse from a pump light source, and outputs detected light pulse having the same repetition frequency as the repetition frequency of the pump light pulse. A signal output device receives the detected light pulse and a probe light pulse from a probe light source, and outputs a signal corresponding to a power of the detected light pulse upon the reception of the probe light pulse. A waveform measurement unit measures a waveform of the output from the signal output device by detecting the output from the signal output device for a period from reception of a trigger signal to reception of a next trigger signal. A first photoelectric conversion unit applies photoelectric conversion to the probe light pulse. A first amplification unit amplifies an output from the first photoelectric conversion unit. A trigger signal output unit outputs a cross-correlation of the output of the first amplification unit and the pump light pulse as the trigger signal. A period difference adjustment unit adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed to the trigger signal output unit. Furthermore, the repetition frequency of the detected light pulse and the repetition frequency of the probe light pulse are different from each other.

According to the second optical measurement device of the present invention, the trigger signal output unit may include: an light modulation unit that modulates the pump light pulse according to the output from the first amplification unit; a photoelectric conversion unit that applies photoelectric conversion to the output from the light modulation unit; an amplification unit that amplifies an output from the photoelectric conversion unit; and a detection unit that detects an output from the amplification unit according to the envelope detection.

According to the second optical measurement device of the present invention, a period from the output of the probe light pulse from the probe light source until the probe light pulse is fed to the signal output device is T1; a period from the output of the pump light pulse from the pump light source until the detected light pulse generated from the output pump light pulse is fed to the signal output device is T2; and the period difference adjustment unit may adjust the period difference so that a value obtained by subtracting the period T3 from the period T4 is equal to a value obtained by subtracting the period T1 from the period T2.

According to the second optical measurement device of the present invention, the period difference adjustment unit may make such an adjustment that the period T4 is equal to the period T2, and the period T3 is equal to the period T1.

According to the second optical measurement device of the present invention, the period difference adjustment unit may cause the periods T4, T2, T3 and T1 are equal to each other.

According to the second optical measurement device of the present invention, the pump light source and the detected light pulse output unit may be connected with each other via an optical fiber; the probe light source and the signal output device may be connected with each other via an optical fiber; the probe light source and the first photoelectric conversion unit may be connected with each other via an optical fiber; and the pump light source and the trigger signal output unit may be connected with each other via an optical fiber.

According to the present invention, a third optical measurement device includes: a detected light pulse output unit that receives a pump light pulse from a pump light source, and outputs detected light pulse having the same repetition frequency as the repetition frequency of the pump light pulse; a signal output device that receives the detected light pulse and a probe light pulse from a probe light source, and outputs a signal corresponding to a power of the detected light pulse upon the reception of the probe light pulse; a waveform measurement unit that measures a waveform of the output from the signal output device by detecting the output from the signal output device for a period from reception of a trigger signal to reception of a next trigger signal; a second photoelectric conversion unit that applies photoelectric conversion to the pump light pulse; a second amplification unit that amplifies an output from the second photoelectric conversion unit a trigger signal output unit that outputs a cross-correlation of the probe light pulse and the output of the second amplification unit as the trigger signal; and a period difference adjustment unit that adjusts a difference in period between a period T3 from the output of the probe light pulse from the probe light source until the probe light pulse is fed to the trigger signal output unit, and a period T4 from the output of the pump light pulse from the pump light source until the pump light pulse is fed, as the output from the second amplification unit, to the trigger signal output unit, wherein the repetition frequency of the detected light pulse and the repetition frequency of the probe light pulse are different from each other.

According to the thus constructed third optical measurement device, a detected light pulse output unit receives a pump light pulse from a pump light source, and outputs detected light pulse having the same repetition frequency as the repetition frequency of the pump light pulse. A signal output device receives the detected light pulse and a probe light pulse from a probe light source, and outputs a signal corresponding to a power of the detected light pulse upon the reception of the probe light pulse. A waveform measurement unit measures a waveform of the output from the signal output device by detecting the output from the signal output device for a period from reception of a trigger signal to reception of a next trigger signal. A second photoelectric conversion unit applies photoelectric conversion to the pump light pulse. A second amplification unit amplifies an output from the second photoelectric conversion unit. A trigger signal output unit outputs a cross-correlation of the probe light pulse and the output of the second amplification unit as the trigger signal. A period difference adjustment unit adjusts a difference in period between a period T3 from the output of the probe light pulse from the probe light source until the probe light pulse is fed to the trigger signal output unit, and a period T4 from the output of the pump light pulse from the pump light source until the pump light pulse is fed, as the output from the second amplification unit, to the trigger signal output unit. Furthermore, the repetition frequency of the detected light pulse and the repetition frequency of the probe light pulse are different from each other.

According to the third optical measurement device of the present invention, the trigger signal output unit may include: an light modulation unit that modulates the probe light pulse according to the output from the second amplification unit; a photoelectric conversion unit that applies photoelectric conversion to the output from the light modulation unit; an amplification unit that amplifies an output from the photoelectric conversion unit; and a detection unit that detects an output from the amplification unit according to the envelope detection.

According to the third optical measurement device of the present invention, a period from the output of the probe light pulse from the probe light source until the probe light pulse is fed to the signal output device is T1; a period from the output of the pump light pulse from the pump light source until the detected light pulse generated from the output pump light pulse is fed to the signal output device is T2; and the period difference adjustment unit may adjust the period difference so that a value obtained by subtracting the period T3 from the period T4 is equal to a value obtained by subtracting the period T1 from the period T2.

According to the third optical measurement device of the present invention, the period difference adjustment unit may make such an adjustment that the period T4 is equal to the period T2, and the period T3 is equal to the period T1.

According to the third optical measurement device of the present invention, the period difference adjustment unit may cause the periods T4, T2, T3 and T1 are equal to each other.

According to the third optical measurement device of the present invention, the pump light source and the detected light pulse output unit may be connected with each other via an optical fiber; the probe light source and the signal output device may be connected with each other via an optical fiber; the probe light source and the trigger signal output unit may be connected with each other via an optical fiber; and the pump light source and the second photoelectric conversion unit may be connected with each other via an optical fiber.

According to the present invention, a first trigger signal generation device includes: a first photoelectric conversion unit that applies photoelectric conversion to the probe light pulse; a second photoelectric conversion unit that applies photoelectric conversion to the pump light pulse; a first amplification unit that amplifies an output from the first photoelectric conversion unit; a second amplification unit that amplifies an output from the second photoelectric conversion unit; a trigger signal output unit that outputs a cross-correlation of outputs of the first amplification unit and the second amplification unit as the trigger signal; and a period difference adjustment unit that adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed, as the output from the second amplification unit, to the trigger signal output unit, wherein the repetition frequency of the pump light pulse and the repetition frequency of the probe light pulse are different from each other.

According to the thus constructed first trigger signal generation device, a first photoelectric conversion unit applies photoelectric conversion to the probe light pulse. A second photoelectric conversion unit applies photoelectric conversion to the pump light pulse. A first amplification unit amplifies an output from the first photoelectric conversion unit. A second amplification unit amplifies an output from the second photoelectric conversion unit. A trigger signal output unit outputs a cross-correlation of outputs of the first amplification unit and the second amplification unit as the trigger signal. A period difference adjustment unit adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed, as the output from the second amplification unit, to the trigger signal output unit. Furthermore, the repetition frequency of the pump light pulse and the repetition frequency of the probe light pulse are different from each other.

According to the first trigger signal generation device of the present invention, the trigger signal output unit may include: an electric modulation unit that modulates the output from the first amplification unit according to the output from the second amplification unit; an amplification unit that amplifies an output from the electric modulation unit; and a detection unit that detects an output from the amplification unit according to the envelope detection.

According to the first trigger signal generation device of the present invention, the probe light source and the first photoelectric conversion unit may be connected with each other via an optical fiber; and the pump light source and the second photoelectric conversion unit may be connected with each other via an optical fiber.

According to the present invention, a second trigger signal generation device includes: a first photoelectric conversion unit that applies photoelectric conversion to the probe light pulse; a first amplification unit that amplifies an output from the first photoelectric conversion unit; a trigger signal output unit that outputs a cross-correlation of the output of the first amplification unit and the pump light pulse as the trigger signal; and a period difference adjustment unit that adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed to the trigger signal output unit, wherein the repetition frequency of the pump light pulse and the repetition frequency of the probe light pulse are different from each other.

According to the thus constructed second trigger signal generation device, a first photoelectric conversion unit applies photoelectric conversion to the probe light pulse. A first amplification unit amplifies an output from the first photoelectric conversion unit. A trigger signal output unit outputs a cross-correlation of the output of the first amplification unit and the pump light pulse as the trigger signal. A period difference adjustment unit adjusts a difference in period between a period T3 from the output of the probe light pulse from the probe light source until the probe light pulse is fed, as the output from the first amplification unit, to the trigger signal output unit, and a period T4 from the output of the pump light pulse from the pump light source until the pump light pulse is fed to the trigger signal output unit. Furthermore, the repetition frequency of the pump light pulse and the repetition frequency of the probe light pulse are different from each other.

According to the second trigger signal generation device of the present invention, the trigger signal output unit may include: an light modulation unit that modulates the pump light pulse according to the output from the first amplification unit; a photoelectric conversion unit that applies photoelectric conversion to the output from the light modulation unit; an amplification unit that amplifies an output from the photoelectric conversion unit; and a detection unit that detects an output from the amplification unit according to the envelope detection.

According to the second trigger signal generation device of the present invention, the probe light source and the first photoelectric conversion unit may be connected with each other via an optical fiber; and the pump light source and the trigger signal output unit may be connected with each other via an optical fiber.

According to the present invention, a third trigger signal generation device includes: a second photoelectric conversion unit that applies photoelectric conversion to a pump light pulse; a second amplification unit that amplifies an output from the second photoelectric conversion unit; a trigger signal output unit that outputs a cross-correlation of a probe light pulse and the output of the second amplification unit as the trigger signal; and a period difference adjustment unit that adjusts a difference in period between a period T3 from the output of the probe light pulse from the probe light source until the probe light pulse is fed to the trigger signal output unit, and a period T4 from the output of the pump light pulse from the pump light source until the pump light pulse is fed, as the output from the second amplification unit, to the trigger signal output unit, wherein the repetition frequency of the pump light pulse and the repetition frequency of the probe light pulse are different from each other.

According to the thus constructed third trigger signal generation device, a second photoelectric conversion unit applies photoelectric conversion to a pump light pulse. A second amplification unit amplifies an output from the second photoelectric conversion unit. A trigger signal output unit outputs a cross-correlation of a probe light pulse and the output of the second amplification unit as the trigger signal. A period difference adjustment unit adjusts a difference in period between a period T3 from the output of the probe light pulse from the probe light source until the probe light pulse is fed to the trigger signal output unit, and a period T4 from the output of the pump light pulse from the pump light source until the pump light pulse is fed, as the output from the second amplification unit, to the trigger signal output unit. Furthermore, the repetition frequency of the pump light pulse and the repetition frequency of the probe light pulse are different from each other.

According to the third trigger signal generation device of the present invention, the trigger signal output unit may include: an light modulation unit that modulates the probe light pulse according to the output from the second amplification unit; a photoelectric conversion unit that applies photoelectric conversion to the output from the light modulation unit; an amplification unit that amplifies an output from the photoelectric conversion unit; and a detection unit that detects an output from the amplification unit according to the envelope detection.

According to the third trigger signal generation device of the present invention, the probe light source and the trigger signal output unit may be connected with each other via an optical fiber; and the pump light source and the second photoelectric conversion unit may be connected with each other via an optical fiber.

BEST MODE FOR CARRYING OUT THE INVENTION

Figure 1:
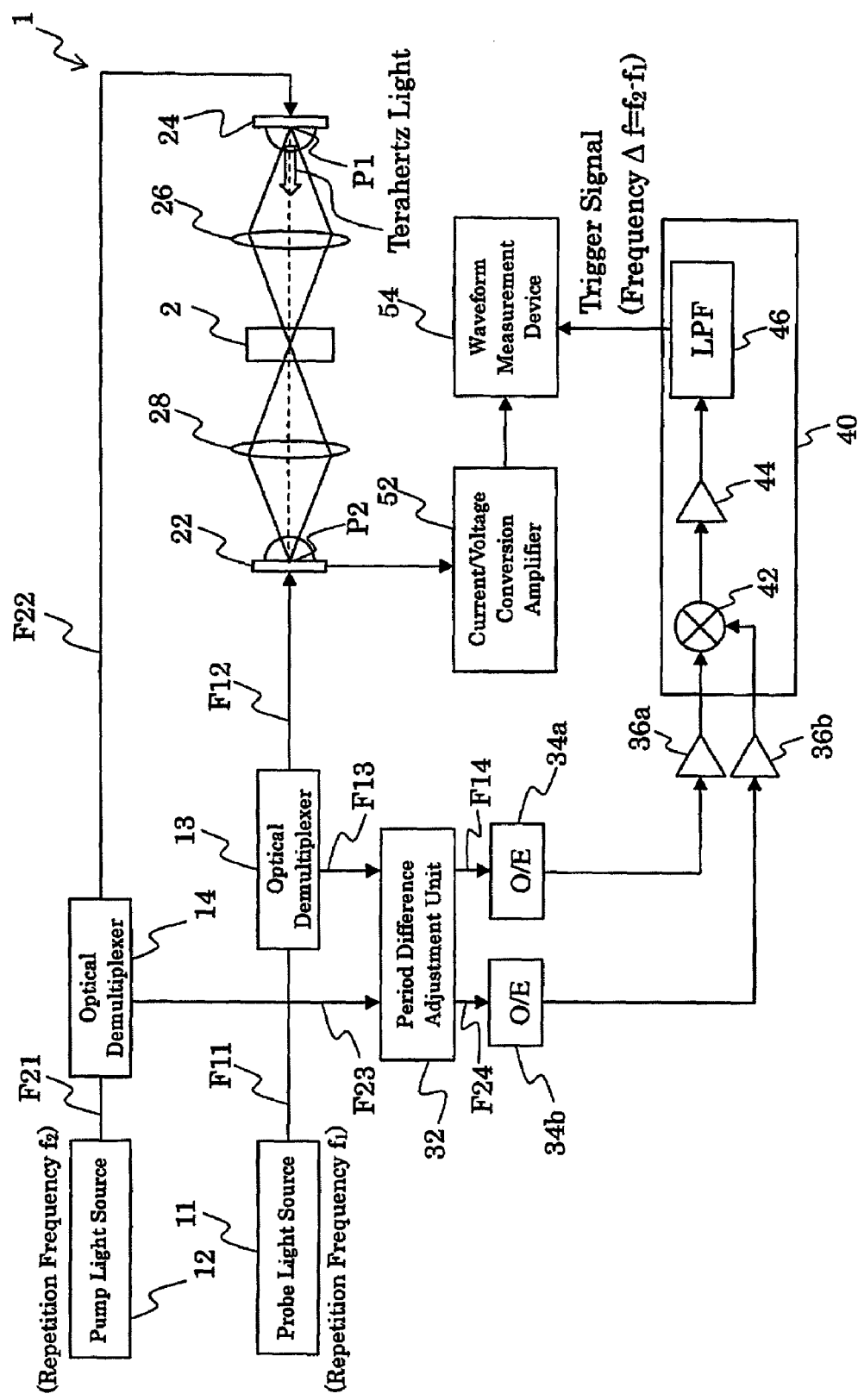
FIG. 1 is a diagram showing a configuration of an optical measurement device 1 according to a first embodiment of the present invention.

A description will now be given of embodiments of the present invention with reference to drawings.
First Embodiment FIG. 1 is a diagram showing a configuration of an optical measurement device 1 according to a first embodiment of the present invention. The optical measurement device 1 according to the first embodiment includes a probe light source 11, a pump light source 12, optical demultiplexers 13 and 14, a signal output device 22, a detected light pulse output unit 24, lenses 26 and 28, a period difference adjustment unit 32, a first photoelectric conversion unit 34a, a second photoelectric conversion unit 34b, a first amplification unit 36a, a second amplification unit 36b, a trigger signal output unit 40, a current/voltage conversion amplifier 52, and a waveform measurement device 54. It should be noted that the optical measurement device 1 measures a terahertz wave which has transmitted through a device under test (DUT) 2.

It should be noted that the period difference adjustment unit 32, the first photoelectric conversion unit 34a, the second photoelectric conversion unit 34b, the first amplification unit 36a, the second amplification unit 36b, and the trigger signal output unit 40 constitute a trigger signal generation device.

The probe light source 11 outputs laser pulse light (probe light pulse) having a pulse width of several tens of femtoseconds and thus having a wavelength in a near infrared area. It should be noted that the repetition frequency of the probe light pulse is $f_1$.

The pump light source 12 outputs laser pulse light (pump light pulse) having a pulse width of several tens of femtoseconds and thus having a wavelength in the near infrared area. It should be noted that the repetition frequency of the pump light pulse is $f_2$. It should be noted that $f_2-f_1=\Delta f>0$. $\Delta f$ is approximately 5 Hz, for example.

The optical demultiplexer 13 receives the probe light pulse from the probe light source 11, and feeds the probe light pulse to the signal output device 22 and the period difference adjustment unit 32. It should be noted that the optical demultiplexer 13 and the probe light source 11 are connected via an optical fiber F11, the optical demultiplexer 13 and the signal output device 22 are connected via an optical fiber F12, and the optical demultiplexer 13 and the period difference adjustment unit 32 are connected via an optical fiber F13. Moreover, the optical demultiplexer 13 is constituted by optical fibers.

Thus, the probe light source 11 and the signal output device 22 are connected via the optical fibers F11 and F12, and the optical demultiplexer 13 (constituted by the optical fibers).

The optical demultiplexer 14 receives the pump light pulse from the pump light source 12, and feeds the pump light pulse to the detected light pulse output unit 24 and the period difference adjustment unit 32. It should be noted that the optical demultiplexer 14 and the pump light source 12 are connected via an optical fiber F21, the optical demultiplexer 14 and the detected light pulse output unit 24 are connected via an optical fiber F22, and the optical demultiplexer 14 and the period difference adjustment unit 32 are connected via an optical fiber F23. Moreover, the optical demultiplexer 14 is constituted by optical fibers.

Thus, the pump light source 12 and the detected light pulse output unit 24 are connected via the optical fibers F21 and F22, and the optical demultiplexer 14 (constituted by the optical fibers).

The detected light pulse output unit 24 receives the pump light pulse from the pump light source 12, and outputs a detected light pulse having the same repetition frequency ($f_2$) as the repetition frequency of the pump light pulse. The detected light pulse output unit 24 is a photoconductive switch, for example. When the pump light pulse is fed to the photoconductive switch, a terahertz light (detected light pulse) is output from the photoconductive switch. Since the structure of the photoconductive switch is widely known, and a description thereof, therefore, is omitted. Moreover, the detected light pulse output unit 24 may be non-liner optical crystal.

It should be noted that the repetition frequency $f_2$ of the detected light pulse and the repetition frequency $f_1$ of the probe light pulse are different from each other.

Moreover, the terahertz light (detected light pulse) is emitted from one point P1 of the detected light pulse output unit 24.

The lens 26 is a convex lens. The terahertz light output from the detected light pulse output unit 24 transmits through the lens 26, and is fed to the DUT 2.

The lens 28 is a convex lens. The terahertz light which has transmitted through the DUT 2 transmits through the lens 28, and is fed to the signal output device 22.

The terahertz light is condensed to one point P2 on the signal output device 22.

The signal output device 22 receives the detected light pulse (terahertz light) and the probe light pulse from the probe light source 11, and outputs a signal corresponding to a power of the detected light pulse upon the reception of the probe light pulse. It should be noted that the signal output device 22 receives the terahertz light via the DUT 2 according to the present embodiment. The signal output device 22 is a photoconductive switch, for example. The signal output from the photoconductive switch is a current. Since the structure of the photoconductive switch is widely known, and a description thereof, therefore, is omitted. Moreover, the signal output device 22 may be non-liner optical crystal.

The first photoelectric conversion unit 34a receives the probe light pulse via the optical demultiplexer 13 and the period difference adjustment unit 32, and applies the photoelectric conversion to the probe light pulse.

The second photoelectric conversion unit 34b receives the pump light pulse via the optical demultiplexer 14 and the period difference adjustment unit 32, and applies the photoelectric conversion to the pump light pulse.

The first amplification unit 36a amplifies an output from the first photoelectric conversion unit 34a. An output from the first amplification unit 36a is fed to the mixer 42. The output from the first amplification unit 36a is large enough to operate the mixer 42.

The second amplification unit 36b amplifies an output from the second photoelectric conversion unit 34b. An output from the second amplification unit 36b is fed to the mixer 42. The output from the second amplification unit 36b is large enough to operate the mixer 42.

The trigger signal output unit 40 outputs a cross-correlation of the outputs of the first amplification unit 36a and the second amplification unit 36b as a trigger signal.

The trigger signal output unit 40 includes a mixer (electric modulation unit) 42, an amplification unit 44, and a low-pass filter (detection unit) 46.

The mixer (electric modulation unit) 42 multiplies the output from the first amplification unit 36a and the output from the second amplification unit 36b by each other, and outputs the result of the multiplication. The frequency of the output from the mixer 42 is a difference $\Delta f$ $(=f_2-f_1)$ between the frequency $f_1$ of the output from the first amplification unit 36a and the frequency $f_2$ of the output from the second amplification unit 36b.

It can be considered that the mixer (electric modulation unit) 42 modulates the output from the first amplification unit 36a according to the output from the second amplification unit 36b.

Moreover, a unit which modulates the output from the first amplification unit 36a according to the output from the second amplification unit 36b can be used in replace of the mixer 42. For example, a switching element which transmits the output from the first amplification unit 36a in proportion to the output voltage of the second amplification unit 36b can be used in place of the mixer 42. Moreover, for example, a comparator which compares the output from the first amplification unit 36a and the output from the second amplification unit 36b with each other and thereby changes an output according to which output is larger can be used in place of the mixer 42.

The amplification unit 44 amplifies the output from the mixer 42.

The low-pass filter (detection unit) 46 passes a low frequency component of an output from the amplification unit 44, and cuts off a high frequency component, thereby applying the envelope detection to the output from the amplification unit 44. An output from the low-pass filter 46 is the trigger signal (frequency $\Delta f(=f_2-f_1)$).

The period difference adjustment unit 32 adjusts a period difference between periods T3 and T4.

It should be noted that the period T3 is a period from when the probe light pulse is output from the probe light source 11 until the probe light pulse is routed through the optical demultiplexer 13, is converted by the first photoelectric conversion unit 34a by means of the photoelectric conversion, and is fed, as the output from the first amplification unit 36a, to the trigger signal output unit 40.

Moreover, the period T4 is a period from when the pump light pulse is output from the pump light source 12 until the pump light pulse is routed through the optical demultiplexer 14, is converted by the second photoelectric conversion unit 34b by means of the photoelectric conversion, and is fed, as the output from the second amplification unit 36b, to the trigger signal output unit 40.

It should be noted that the period difference adjustment unit 32 and the first photoelectric conversion unit 34a are connected with each other via an optical fiber F14. The period difference adjustment unit 32 and the second photoelectric conversion unit 34b are connected with each other via an optical fiber F24.

The period difference adjustment unit 32 receives the probe light pulse and the pump light pulse, delays either one or both of them, and feeds them respectively to the first photoelectric conversion unit 34a and the second photoelectric conversion unit 34b. The period difference adjustment unit 32 may be an optical fiber having a predetermined length, for example.

For example, if the optical fiber F13 and the optical fiber F14 are connected with each other via an optical fiber with a predetermined length, and the optical fiber F23 and the optical fiber F24 are directly connected with each other, the probe light pulse is to be delayed. If the optical fiber F23 and the optical fiber F24 are connected with each other via an optical fiber with a predetermined length, and the optical fiber F13 and the optical fiber F14 are directly connected with each other, the pump light pulse is to be delayed. If the optical fiber F13 and the optical fiber F14 are connected with each other via an optical fiber with a predetermined length, and the optical fiber F23 and the optical fiber F24 are connected with each other via an optical fiber with a further predetermined length, the probe light pulse and the pump light pulse are to be delayed.

The probe light source 11 and the first photoelectric conversion unit 34a are connected with each other via the optical fibers F11, F13 and F14, and the period difference adjustment unit 32 (optical fiber). The pump light source 12 and the second photoelectric conversion unit 34b are connected with each other via the optical fibers F21, F23 and F24, and the period difference adjustment unit 32 (optical fiber).

It should be noted that the period difference adjustment unit 32 adjusts the period difference between the period T3 and the period T4 such that a value obtained by subtracting the period T3 from the period T4 is equal to a value obtained by subtracting a period T1 from a period T2.

For example, the period difference adjustment unit 32 makes such an adjustment that the period T4 is equal to the period T2, and the period T3 is equal to the period T1. Alternatively, the periods T4, T2, T3 and T1 are equal to each other (T4=T2=T3=T1).

It should be noted that the period T1 is a period from when the probe light pulse is output from the probe light source 11 until the probe light pulse is routed through the optical demultiplexer 13 and is fed to the signal output device 22.

Moreover, the period T2 is a period from when the pump light pulse is output from the pump light source 12 until the pump light pulse is routed through the optical demultiplexer 14, and reaches the detected light pulse output unit 24, and the detected light pulse (terahertz light) generated by the output pump light pulse is fed to the signal output device 22.

It should be noted that a period T22 from when the detected light pulse is output until the detected light pulse is fed to the signal output device 22 is calculated assuming that the detected light pulse passes on a straight line connecting between the points P1 and P2. By adding, to this period T22, a period T21 from when the pump light pulse is output from the pump light source 12 until the pump light pulse reaches the detected light pulse output unit 24, the period T2 can be obtained (T2=T21+T22).

The current/voltage conversion amplifier 52 converts a current output from the signal output device 22 into a voltage, and amplifies the voltage. It should be noted that the current/voltage conversion amplifier 52 includes a low-pass filter, and applies the envelope detection to the amplified voltage, and outputs a result to the waveform measurement device 54.

The waveform measurement device 54 measures a waveform of the output from the signal output device 22 by detecting the output from the signal output device 22 during a period between reception of a trigger signal and reception of a next trigger signal. The waveform measurement device 54 is a digital oscilloscope, for example.

Figure 2:
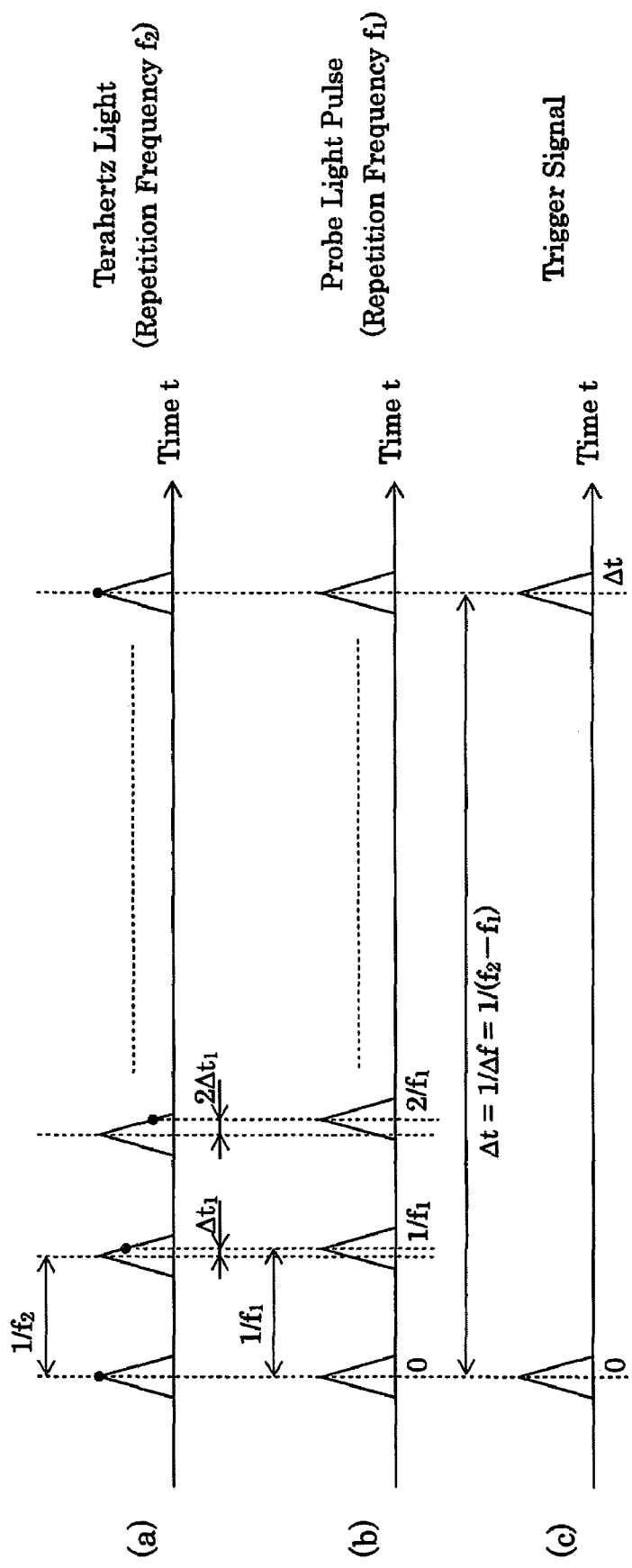
FIGS. 2(a) to 2(c) are time charts of the terahertz light (detected light pulse (FIG. 2(a))), the probe light pulse (FIG. 2(b)), and the trigger signal (FIG. 2(c))

FIGS. 2(*a*) to 2(*c*) are time charts of the terahertz light (detected light pulse (FIG. 2(*a*))), the probe light pulse (FIG. 2(*b*)), and the trigger signal (FIG. 2(*c*)).

The signal output device 22 outputs the current corresponding to the power of the terahertz light at a time point when the optical power of the probe light pulse takes the maximum. For example, the signal output device 22 outputs the current corresponding to the power of the terahertz light at time points $t=0, 1/f_1, 2/f_1, \ldots$. In other words, the signal output device 22 outputs the current corresponding to the power of the terahertz light at time points $(0, \Delta t1, 2\Delta t1, \ldots)$ displaced respectively by integer multiples of $\Delta t1$ $(=1/f_1-1/f_2)$ from the time point when the power of the terahertz light takes the maximum. The signal output device 22 outputs the current corresponding to the power of the terahertz light when the displacement from the time point maximizing the power of the terahertz light becomes $1/f_2$ later (refer to a pulse at the right end in FIG. 2(*a*)). At this time point, the measurement of the pulse of the terahertz light for one period has been completed. The period $\Delta t$ required for the completion of measurement for one period of the pulse of the terahertz light is represented as $\Delta t=1/\Delta f=1/(f_2-f_1)$.

It is thus possible to measure the waveform for one period of the output from the signal output device 22 by detecting the output from the signal output device 22 in the period from reception of a trigger signal (t=0) until reception of a next trigger signal (t=Δt).

A description will now be given of an operation of the first embodiment.

The pump light pulse (repetition frequency: $f_2$) is output from the pump light source 12, and is fed to the detected light pulse output unit 24. The detected light pulse (repetition frequency: $f_2$) (such as terahertz light) is output from the detected light pulse output unit 24.

The terahertz light transmits through the lens 26, and is fed to the DUT 2. The terahertz light transmits through the DUT 2 and the lens 28, and is fed to the signal output device 22.

The signal output device 22 receives the probe light pulse (repetition frequency: $f_1$) from the probe light source 11. The signal output device 22, upon the reception of the probe light pulse, outputs the signal (for example, current) corresponding to the power of the detected light pulse (refer to FIGS. 2(*a*) and 2(*b*)). This current is converted into the voltage, is amplified, is further detected by the envelope detection, and is output to the waveform measurement device 54 by the current/voltage conversion amplifier 52.

The probe light pulse output from the probe light source 11 is fed, via the optical demultiplexer 13 and the period difference adjustment unit 32, to the first photoelectric conversion unit 34*a*. The probe light pulse is converted by the first photoelectric conversion unit 34*a* by means of the photoelectric conversion, is further amplified by the first amplification unit 36*a*, and is fed to the mixer 42.

The pump light pulse output from the pump light source 12 is fed, via the optical demultiplexer 14 and the period difference adjustment unit 32, to the second photoelectric conversion unit 34*b*. The pump light pulse is converted by the second photoelectric conversion unit 34*b* by means of the photoelectric conversion, is further amplified by the second amplification unit 36*b*, and is fed to the mixer 42.

The mixer 42 multiplies the output from the first amplification unit 36*a* and the output from the second amplification unit 36*b* by each other, and outputs the result of the multiplication. The output from the mixer 42 is amplified by the amplification unit 44, is detected by the low-pass filer 46 by means of the envelope detection, and is output (refer to FIG. 2(*c*)). This output is to be the trigger signal.

The waveform measurement device 54 measures a waveform of the output from the signal output device 22 by detecting the output from the signal output device 22 during a period between the reception of a trigger signal and the reception of a next trigger signal.

On this occasion, the period difference adjustment unit 32 adjusts the period difference between the period T3 and the period T4 such that the value obtained by subtracting the period T3 from the period T4 is equal to the value obtained by subtracting the period T1 from the period T2. For example, the period difference adjustment unit 32 makes such an adjustment that the period T4 is equal to the period T2, and the period T3 is equal to the period T1. Alternatively, the periods T4, T2, T3 and T1 are equal to each other (T4=T2=T3=T1).

According to the first embodiment, the period difference adjustment unit 32 adjusts the period difference between the period T3 and the period T4 such that the value obtained by subtracting the period T3 from the period T4 is equal to the value obtained by subtracting a period T1 from the period T2. Thus, a difference between a jitter contained in the trigger signal and a jitter contained in the detected light pulse decreases, which enables restraint of a jitter contained in the measured result of the detected light pulse.

According to the first embodiment, the period difference adjustment unit 32 delays either one or both of the probe light pulse and the pump light pulse. However, as a variation of the first embodiment, the period difference adjustment unit 32 may delay either one or both of the outputs from the first photoelectric conversion unit 34*a* and the second photoelectric conversion unit 34*b*.

Figure 3:
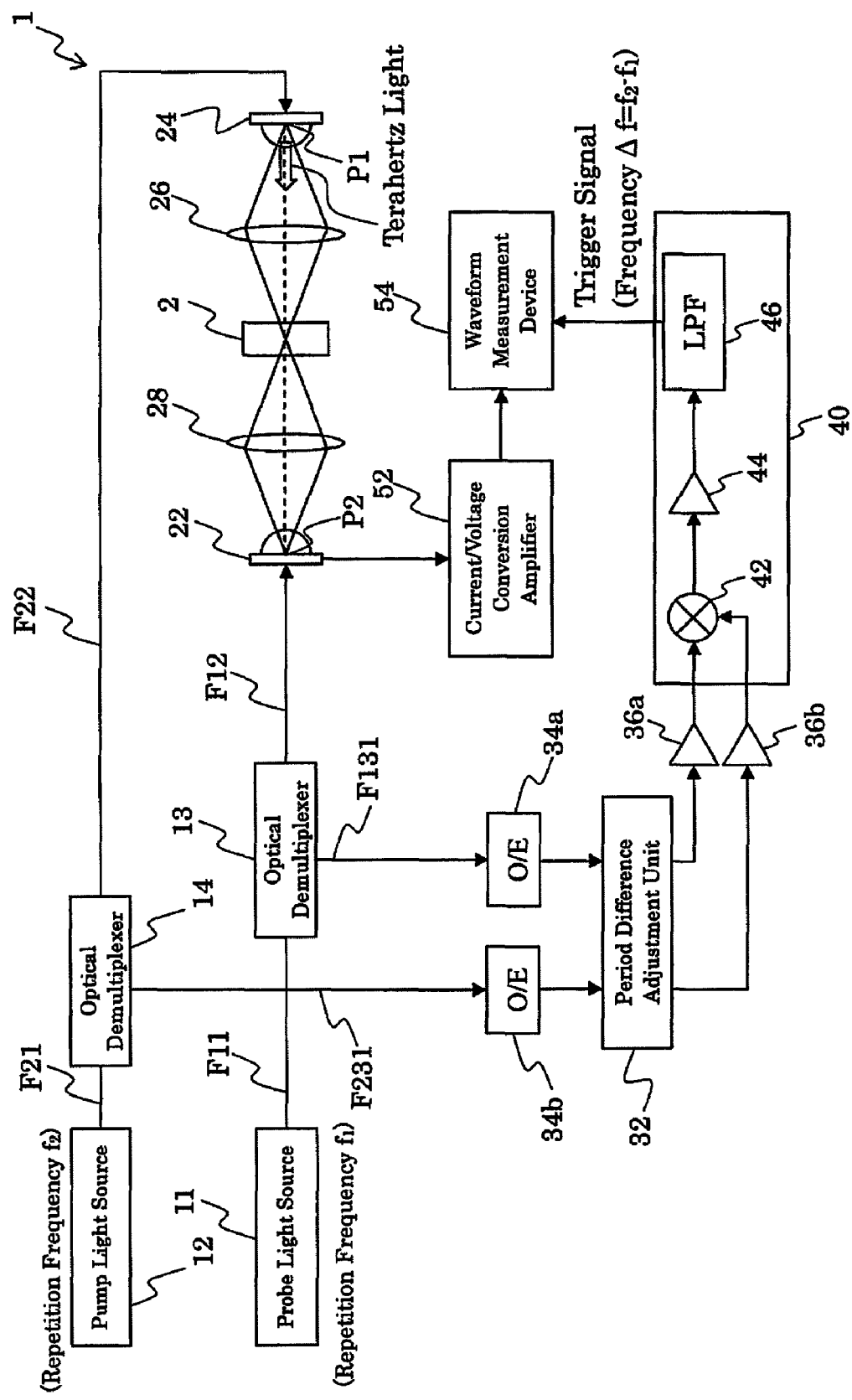
FIG. 3 is a diagram showing a configuration of the optical measurement device 1 according to the variation of the first embodiment.

FIG. 3 is a diagram showing a configuration of the optical measurement device 1 according to the variation of the first embodiment.

The optical demultiplexer 13 and the first photoelectric conversion unit 34*a* are connected with each other via an optical fiber F131. The optical demultiplexer 14 and the second photoelectric conversion unit 34*b* are connected with each other via an optical fiber F231. The period difference adjustment unit 32 receives the outputs from the first photoelectric conversion unit 34*a* and the second photoelectric conversion unit 34*b*, delays either one or both of them, and feeds respective of them to the first amplification unit 36*a* and the second amplification unit 36*b*.

The fact that the period difference adjustment unit 32 makes the adjustment so that the value obtained by subtracting the period T3 from the period T4 is equal to the value obtained by subtracting the period T1 from the period T2 (for example, the adjustment so that the period T4 is equal to the period T2 and the period T3 is equal to the period T1, or the adjustment so that T4=T2=T3=T1) according to the variation of the first embodiment is the same as the first embodiment.

Second Embodiment

The optical measurement device 1 according to a second embodiment is different from the optical measurement device 1 according to the first embodiment in that the pump light is fed to a trigger signal output unit 60 without the photoelectric conversion.

Figure 4:
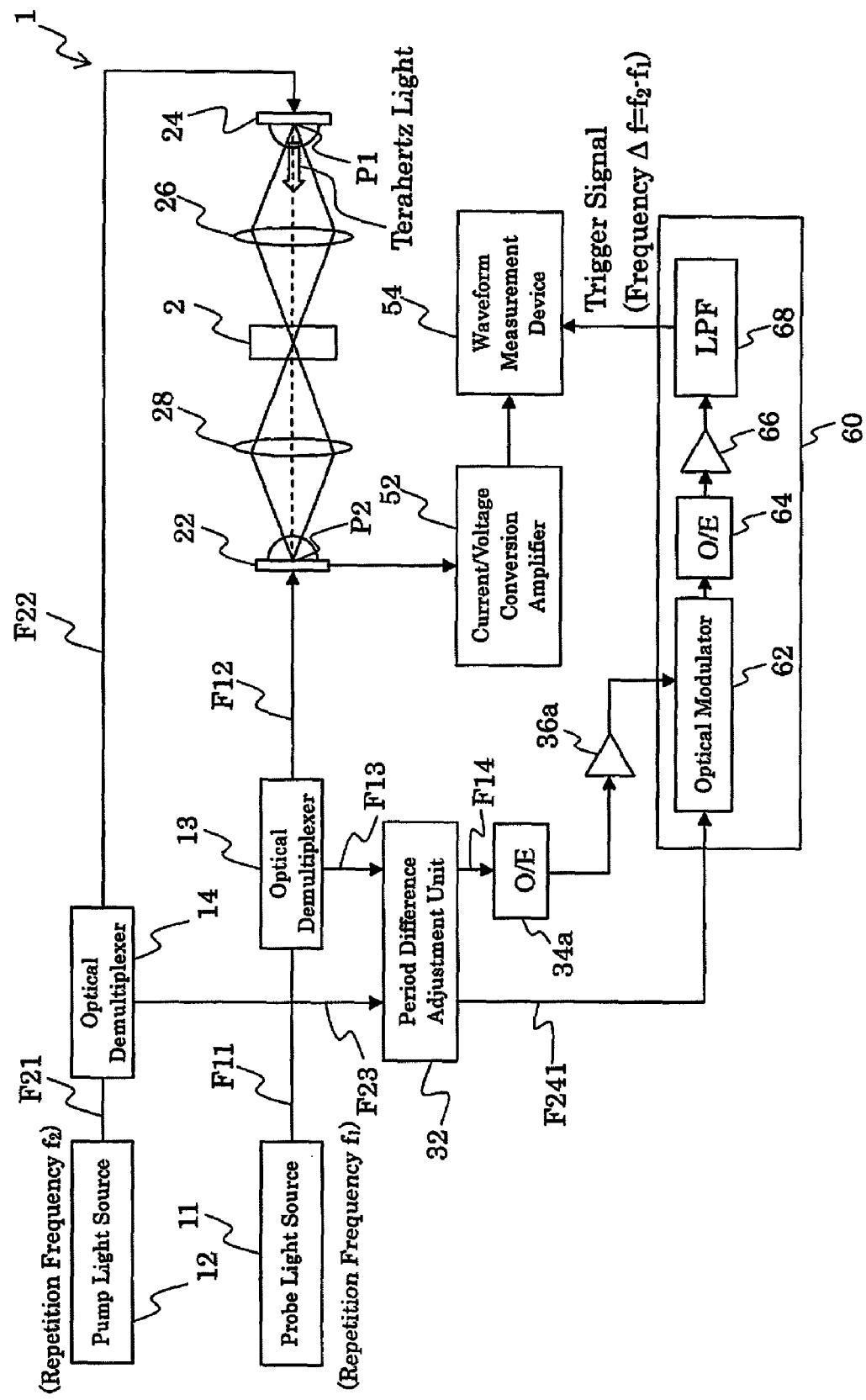
FIG. 4 is a diagram showing a configuration of the optical measurement device 1 according to the second embodiment of the present invention.

FIG. 4 is a diagram showing a configuration of the optical measurement device 1 according to the second embodiment of the present invention. The optical measurement device 1 according to the second embodiment includes the probe light source 11, the pump light source 12, the optical demultiplexers 13 and 14, the signal output device 22, the detected light pulse output unit 24, the lenses 26 and 28, the period difference adjustment unit 32, the first photoelectric conversion unit 34*a*, the first amplification unit 36*a*, the current/voltage conversion amplifier 52, the waveform measurement device 54, and the trigger signal output unit 60. It should be noted that the optical measurement device 1 measures a terahertz wave which has transmitted through the DUT 2. In the following section, the same components are denoted by the same numerals as of the first embodiment, and will be explained in no more details.

It should be noted that the period difference adjustment unit 32, the first photoelectric conversion unit 34*a*, the first amplification unit 36*a*, and the trigger signal output unit 60 constitute the trigger signal generation device.

The probe light source 11, the pump light source 12, the optical demultiplexers 13 and 14, the signal output device 22, the detected light pulse output unit 24, the lenses 26 and 28, the first photoelectric conversion unit 34*a*, the first amplification unit 36*a*, the current/voltage conversion amplifier 52, and the waveform measurement device 54 are the same as those of the first embodiment, and will be explained in no more details. It should be noted that an output from the first amplification unit 36*a* is large enough to operate an optical modulator 62.

The optical measurement device 1 is not provided with the second photoelectric conversion unit 34*b* and the second amplification unit 36*b*, which is different from the first embodiment.

The period difference adjustment unit 32 adjusts a period difference between periods T3 and T4.

The definition of the period T3 is the same as that of the first embodiment, and a description thereof, therefore, is omitted.

The period T4 is a period from when the pump light pulse is output from the pump light source 12 until the pump light pulse is routed through the optical demultiplexer 14 and is fed to the trigger signal output unit 60.

It should be noted that the period difference adjustment unit 32 and the trigger signal output unit 60 are connected with each other via the optical fiber F241.

The period difference adjustment unit 32 receives the probe light pulse and the pump light pulse, delays either one or both of them, and feeds them to the first photoelectric conversion unit 34*a* and the trigger signal output unit 60. The period difference adjustment unit 32 may be an optical fiber having a predetermined length as in the first embodiment, for example.

The probe light source 11 and the first photoelectric conversion unit 34*a* are connected with each other via the optical fibers F11, F13 and F14, and the period difference adjustment unit 32 (optical fiber). The pump light source 12 and the trigger signal output unit 60 are connected with each other via the optical fibers F21, F23 and F241, and the period difference adjustment unit 32 (optical fiber).

It should be noted that the period difference adjustment unit 32 adjusts the period difference between the period T3 and the period T4 such that a value obtained by subtracting the period T3 from the period T4 is equal to a value obtained by subtracting a period T1 from a period T2.

For example, the period difference adjustment unit 32 makes such an adjustment that the period T4 is equal to the period T2, and the period T3 is equal to the period T1. Alternatively, the periods T4, T2, T3 and T1 are equal to each other (T4=T2=T3=T1).

The definitions of the periods T1 and T2 are the same as those of the first embodiment, and a description thereof, therefore, is omitted.

The trigger signal output unit 60 includes the optical modulator 62, a photoelectric conversion unit 64, an amplification unit 66, and a low-pass filter (detection unit) 68.

The trigger signal output unit 60 outputs a cross-correlation of the output from the first amplification unit 36*a* and the pump light pulse.

The optical modulator 62 modulates the pump light pulse according to the output from the first amplification unit 36*a*. For example, the optical modulator 62 changes the power of the pump light pulse to be transmitted in proportion to the output voltage of the first amplification unit 36*a*. It should be noted that a switching element or a comparator can be used in place of the optical modulator 62 as long as it modulates the pump light pulse according to the output from the first amplification unit 36*a*.

The photoelectric conversion unit 64 coverts the output from the optical modulator 62 by means of the photoelectric conversion.

The amplification unit 66 amplifies the output from the photoelectric conversion unit 64.

The low-pass filter (detection unit) 68 passes a low frequency component of an output from the amplification unit 66, and cuts off a high frequency component, thereby applying the envelope detection to the output from the amplification unit 66. An output from the low-pass filter 66 is the trigger signal (frequency $\Delta f(=f_2-f_1)$).

A description will now be given of an operation of the second embodiment.

The pump light pulse (repetition frequency: $f_2$) is output from the pump light source 12, and is fed to the detected light pulse output unit 24. The detected light pulse (repetition frequency: $f_2$) (such as terahertz light) is output from the detected light pulse output unit 24.

The terahertz light passes through the lens 26, and is fed to the DUT 2. The terahertz light transmits through the DUT 2 and the lens 28, and is fed to the signal output device 22.

The signal output device 22 receives the probe light pulse (repetition frequency: $f_1$) from the probe light source 11. The signal output device 22, upon the reception of the probe light pulse, outputs the signal (for example, current) corresponding to the power of the detected light pulse (refer to FIGS. 2(*a*) and 2(*b*)). This current is converted into the voltage, is amplified, is further detected by the envelope detection, and is output to the waveform measurement device 54 by the current/voltage conversion amplifier 52.

The probe light pulse output from the probe light source 11 is fed, via the optical demultiplexer 13 and the period difference adjustment unit 32, to the first photoelectric conversion unit 34*a*. The probe light pulse is converted by the first photoelectric conversion unit 34*a* by means of the photoelectric conversion, is further amplified by the first amplification unit 36*a*, and is fed to the optical modulator 62.

The pump light pulse output from the pump light source 12 is fed, via the optical demultiplexer 14 and the period difference adjustment unit 32, to the optical modulator 62 of the trigger signal output unit 60.

The optical modulator 62 modulates the pump light pulse according to the output from the first amplification unit 36*a*.

Figure 5:
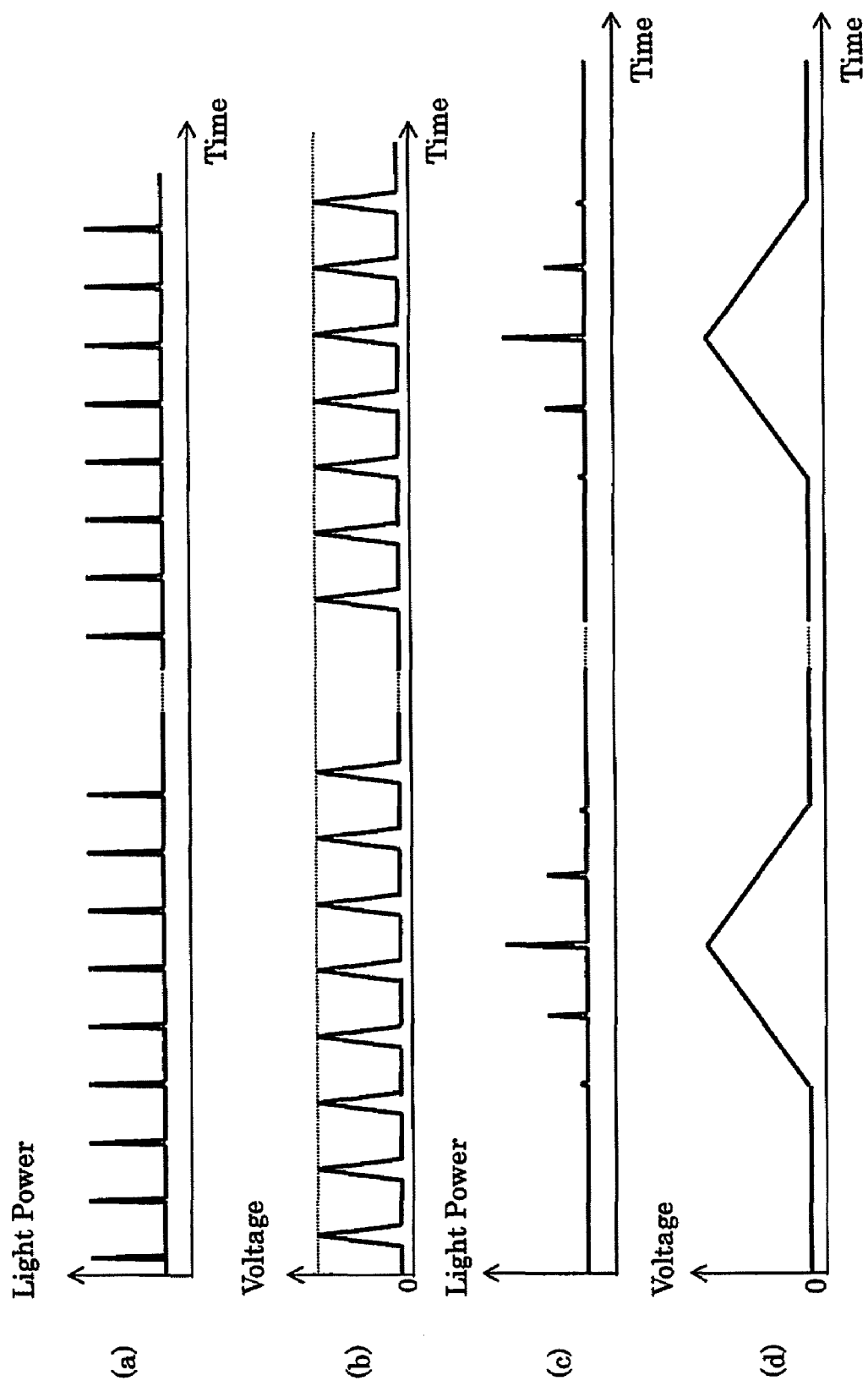
FIGS. 5(a) to 5(d) are time charts of the pump light pulse fed to the optical modulator 62 (FIG. 5(a)), the electric signal output from the first amplification unit 36a (FIG. 5(b)), the output from the optical modulator 62 (FIG. 5(c)), and the output from the low-pass filter 68 (FIG. 5(d))

FIGS. 5(*a*) to 5(*d*) are time charts of the pump light pulse fed to the optical modulator 62 (FIG. 5(*a*)), the electric signal output from the first amplification unit 36*a* (FIG. 5(*b*)), the output from the optical modulator 62 (FIG. 5(*c*)), and the output from the low-pass filter 68 (FIG. 5(*d*)).

The output from the optical modulator 62 (FIG. 5(c)) corresponds to the electric signal which is output from the first amplification unit 36a (FIG. 5(b)) and sampled according to the pump light pulse (FIG. 5(a)).

The output from the optical modulator 62 is converted by the photoelectric conversion unit 64 by means of the photoelectric conversion, is amplified by the amplification unit 66, and is fed to the low-pass filter 68. The low-pass filter 68 detects the output from the amplification unit 66 by means of the envelope detection (FIG. 5(d)), and outputs the result of the envelope detection. This output is to be the trigger signal.

The waveform measurement device 54 measures a waveform of the output from the signal output device 22 by detecting the output from the signal output device 22 during a period between the reception of a trigger signal and the reception of a next trigger signal.

On this occasion, the period difference adjustment unit 32 adjusts the period difference between the period T3 and the period T4 such that the value obtained by subtracting the period T3 from the period T4 is equal to the value obtained by subtracting the period T1 from the period T2. For example, the period difference adjustment unit 32 makes such an adjustment that the period T4 is equal to the period T2, and the period T3 is equal to the period T1. Alternatively, the periods T4, T2, T3 and T1 are equal to each other (T4=T2=T3=T1).

According to the second embodiment, there are obtained the same effects as in the first embodiment.

According to the second embodiment, the period difference adjustment unit 32 delays either one or both of the probe light pulse and the pump light pulse. However, as a variation of the second embodiment, a period difference adjustment unit 32a may delay the output from the first photoelectric conversion unit 34a, and a period difference adjustment unit 32b may delay the pump light pulse. Though both the period difference adjustment units 32a and 32b may exist, only either one of them may exist.

Figure 6:
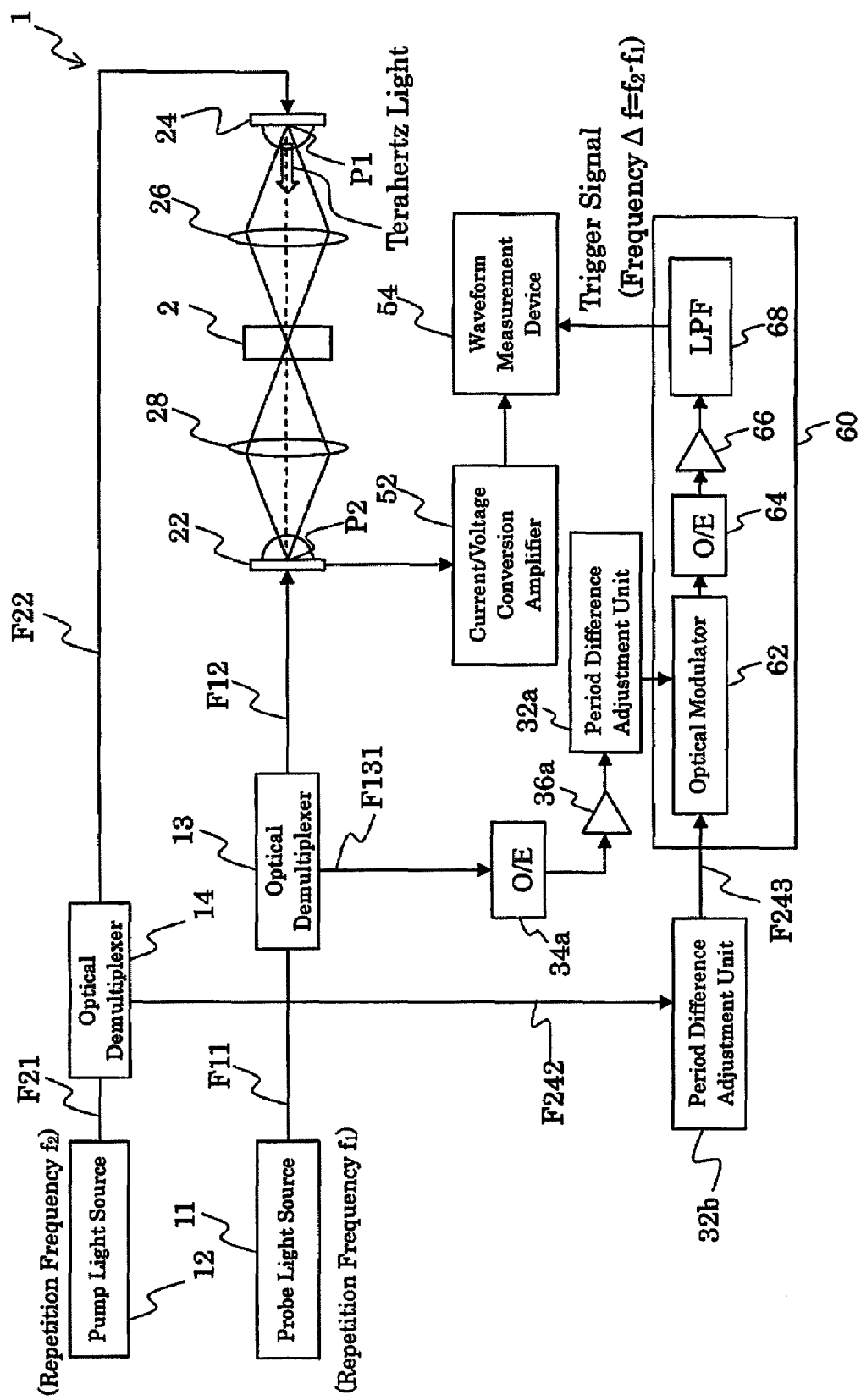
FIG. 6 is a diagram showing a configuration of the optical measurement device 1 according to the variation of the second embodiment.

FIG. 6 is a diagram showing a configuration of the optical measurement device 1 according to the variation of the second embodiment.

The optical demultiplexer 13 and the first photoelectric conversion unit 34a are connected with each other via an optical fiber F131. The optical demultiplexer 14 and the period difference adjustment unit 32b are connected with each other via an optical fiber F242. It should be noted that the period difference adjustment unit 32b and the trigger signal output unit 60 are connected with each other via an optical fiber F243.

The period difference adjustment unit 32a receives and delays the output from the first photoelectric conversion unit 34a (via the first amplification unit 36a), and feeds the delayed output to the trigger signal output unit 60.

The period difference adjustment unit 32b receives and delays the pump light pulse, and feeds the delayed pump light pulse to the trigger signal output unit 60.

The fact that the period difference adjustment units 32a and 32b make the adjustment so that the value obtained by subtracting the period T3 from the period T4 is equal to the value obtained by subtracting the period T1 from the period T2 (for example, the adjustment so that the period T4 is equal to the period T2 and the period T3 is equal to the period T1, or the adjustment so that T4=T2=T3=T1) according to the variation of the second embodiment is the same as the period difference adjustment unit 32 according to the second embodiment.

Third Embodiment

The optical measurement device 1 according to a third embodiment is different from the optical measurement device 1 according to the first embodiment in that the probe light is fed to the trigger signal output unit 60 without the photoelectric conversion.

Figure 7:
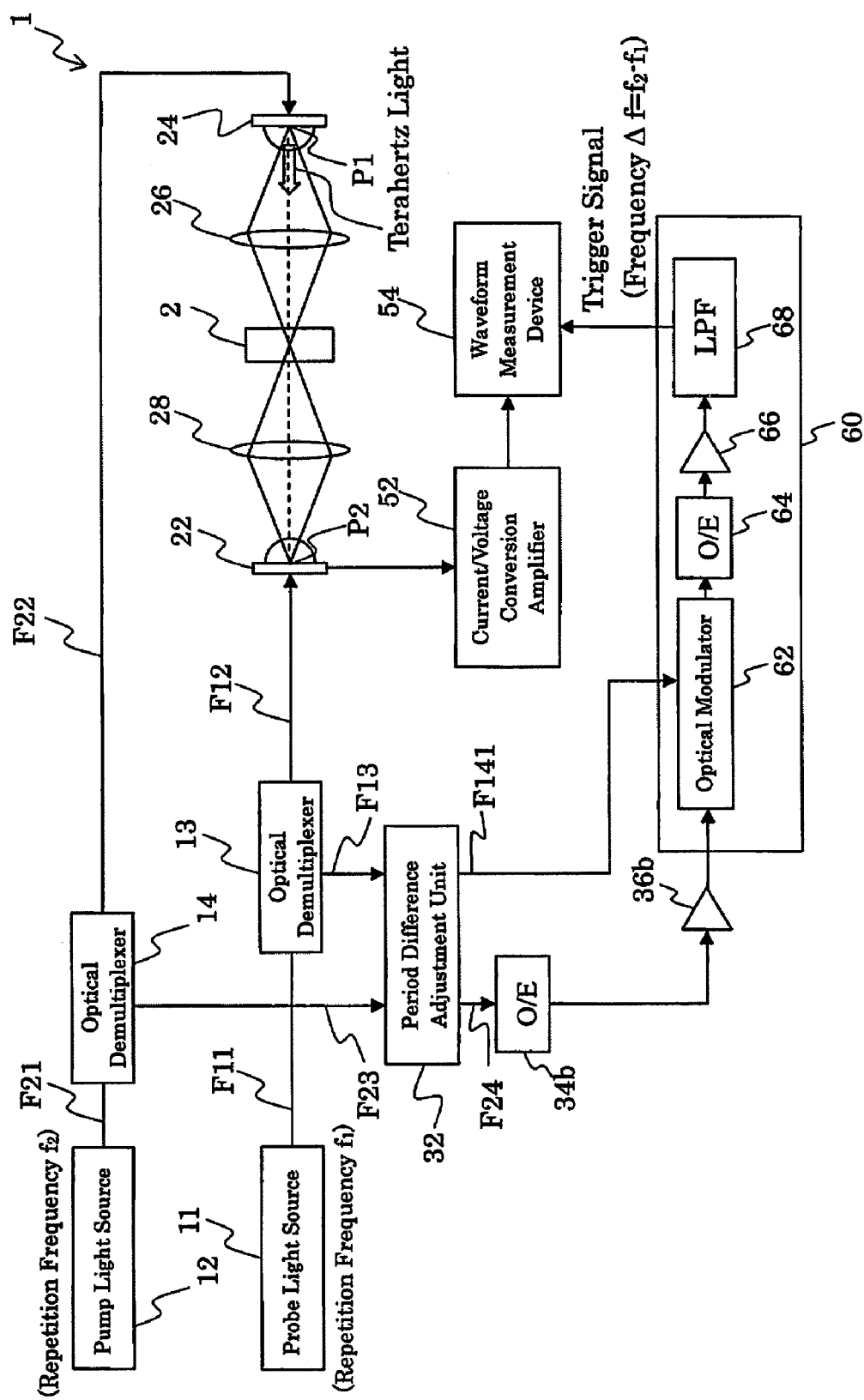
FIG. 7 is a diagram showing a configuration of the optical measurement device 1 according to the third embodiment of the present invention.

FIG. 7 is a diagram showing a configuration of the optical measurement device 1 according to the third embodiment of the present invention. The optical measurement device 1 according to the third embodiment includes the probe light source 11, the pump light source 12, the optical demultiplexers 13 and 14, the signal output device 22, the detected light pulse output unit 24, the lenses 26 and 28, the period difference adjustment unit 32, the second photoelectric conversion unit 34b, the second amplification unit 36b, the current/voltage conversion amplifier 52, the waveform measurement device 54, and the trigger signal output unit 60. It should be noted that the optical measurement device 1 measures a terahertz wave which has transmitted through the DUT 2. In the following section, the same components are denoted by the same numerals as of the first embodiment, and will be explained in no more details.

It should be noted that the period difference adjustment unit 32, the second photoelectric conversion unit 34b, the second amplification unit 36b, and the trigger signal output unit 60 constitute the trigger signal generation device.

The probe light source 11, the pump light source 12, the optical demultiplexers 13 and 14, the signal output device 22, the detected light pulse output unit 24, the lenses 26 and 28, the second photoelectric conversion unit 34b, the second amplification unit 36b, the current/voltage conversion amplifier 52, and the waveform measurement device 54 are the same as those of the first embodiment, and will be explained in no more details. It should be noted that an output from the second amplification unit 36b is large enough to operate the optical modulator 62.

The optical measurement device 1 is not provided with the first photoelectric conversion unit 34a and the first amplification unit 36a, which is different from the first embodiment.

The period difference adjustment unit 32 adjusts a period difference between periods T3 and T4.

The definition of the period T4 is the same as that of the first embodiment, and a description thereof, therefore, is omitted.

The period T3 is a period from when the probe light pulse is output from the probe light source 11 until the probe light pulse is routed through the optical demultiplexer 13 and is fed to the trigger signal output unit 60.

It should be noted that the period difference adjustment unit 32 and the trigger signal output unit 60 are connected with each other via an optical fiber F141.

The period difference adjustment unit 32 receives the probe light pulse and the pump light pulse, delays either one or both of them, and feeds them to the trigger signal output unit 60 and the second photoelectric conversion unit 34b. The period difference adjustment unit 32 may be an optical fiber having a predetermined length as in the first embodiment, for example.

The probe light source 11 and the trigger signal output unit 60 are connected with each other via the optical fibers F11, F13 and F141, and the period difference adjustment unit 32 (optical fiber). The pump light source 12 and the second photoelectric conversion unit 34b are connected with each other via the optical fibers F21, F23 and F24, and the period difference adjustment unit 32 (optical fiber).

It should be noted that the period difference adjustment unit 32 adjusts the period difference between the period T3 and the period T4 such that a value obtained by subtracting the period T3 from the period T4 is equal to a value obtained by subtracting a period T1 from a period T2.

For example, the period difference adjustment unit 32 makes such an adjustment that the period T4 is equal to the period T2, and the period T3 is equal to the period T1. Alternatively, the periods T4, T2, T3 and T1 are equal to each other (T4=T2=T3=T1).

The definitions of the periods T1 and T2 are the same as those of the first embodiment, and a description thereof, therefore, is omitted.

The trigger signal output unit 60 includes the optical modulator 62, the photoelectric conversion unit 64, the amplification unit 66, and the low-pass filter (detection unit) 68.

The trigger signal output unit 60 outputs a cross-correlation of the outputs of the probe light pulse and the second amplification unit 36b as a trigger unit.

The optical modulator 62 modulates the probe light pulse according to the output from the second amplification unit 36b. For example, the optical modulator 62 changes the power of the probe light pulse to be transmitted in proportion to the output from the second amplification unit 36b. It should be noted that a switching element or a comparator can be used in place of the optical modulator 62 as long as it modulates the probe light pulse according to the output from the second amplification unit 36b.

The photoelectric conversion unit 64, the amplification unit 66, and the low-pass filter (detection unit) 68 are the same as those of the second embodiment, and a description thereof, therefore, is omitted.

A description will now be given of an operation of the third embodiment.

The pump light pulse (repetition frequency: $f_2$) is output from the pump light source 12, and is fed to the detected light pulse output unit 24. The detected light pulse (repetition frequency: $f_2$) (such as terahertz light) is output from the detected light pulse output unit 24.

The terahertz light passes through the lens 26, and is fed to the DUT 2. The terahertz light transmits through the DUT 2 and the lens 28, and is fed to the signal output device 22.

The signal output device 22 receives the probe light pulse (repetition frequency: $f_1$) from the probe light source 11. The signal output device 22, upon the reception of the probe light pulse, outputs the signal (for example, current) corresponding to the power of the detected light pulse (refer to FIGS. 2(a) and 2(b)). This current is converted into the voltage, is amplified, is further detected by the envelope detection, and is output to the waveform measurement device 54 by the current/voltage conversion amplifier 52.

The probe light pulse output from the probe light source 11 is fed, via the optical demultiplexer 13 and the period difference adjustment unit 32, to the optical modulator 62 of the trigger signal output unit 60.

The pump light pulse output from the pump light source 12 is fed, via the optical demultiplexer 14 and the period difference adjustment unit 32, to the second photoelectric conversion unit 34b. The pump light pulse is converted by the second photoelectric conversion unit 34b by means of the photoelectric conversion, is further amplified by the second amplification unit 36b, and is fed to the optical modulator 62.

The optical modulator 62 modulates the probe light pulse according to the output from the second amplification unit 36b.

The output from the optical modulator 62 is converted by the photoelectric conversion unit 64 by means of the photoelectric conversion, is amplified by the amplification unit 66, and is fed to the low-pass filter 68. The low-pass filter 68 detects the output from the amplification unit 66 by means of the envelope detection, and outputs the result of the envelope detection. This output is to be the trigger signal.

The waveform measurement device 54 measures a waveform of the output from the signal output device 22 by detecting the output from the signal output device 22 during a period between the reception of a trigger signal and the reception of a next trigger signal.

On this occasion, the period difference adjustment unit 32 adjusts the period difference between the period T3 and the period T4 such that the value obtained by subtracting the period T3 from the period T4 is equal to the value obtained by subtracting the period T1 from the period T2. For example, the period difference adjustment unit 32 makes such an adjustment that the period T4 is equal to the period T2, and the period T3 is equal to the period T1. Alternatively, the periods T4, T2, T3 and T1 are equal to each other (T4=T2=T3=T1).

According to the third embodiment, there are obtained the same effects as in the first embodiment.

According to the third embodiment, the period difference adjustment unit 32 delays either one or both of the probe light pulse and the pump light pulse. However, as a variation of the third embodiment, the period difference adjustment unit 32a may delay the probe light pulse, and the period difference adjustment unit 32b may delay the output from the second photoelectric conversion unit 34b. Though both the period difference adjustment units 32a and 32b may exist, only either one of them may exist.

Figure 8:
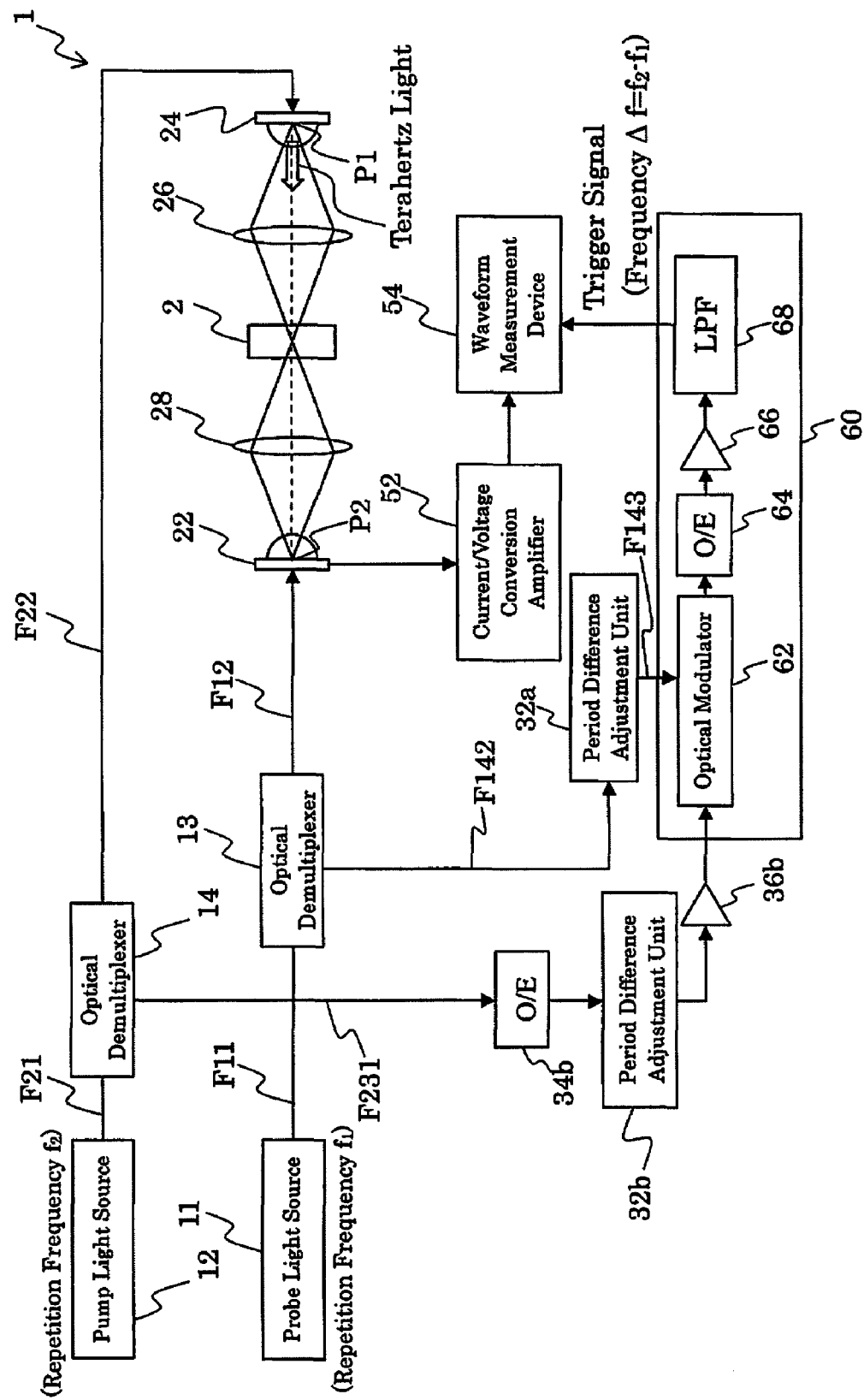
FIG. 8 is a diagram showing a configuration of the optical measurement device 1 according to the variation of the third embodiment.

FIG. 8 is a diagram showing a configuration of the optical measurement device 1 according to the variation of the third embodiment.

The optical demultiplexer 14 and the second photoelectric conversion unit 34b are connected with each other via the optical fiber F231. The optical demultiplexer 13 and the period difference adjustment unit 32a are connected with each other via an optical fiber F142. It should be noted that the period difference adjustment unit 32a and the trigger signal output unit 60 are connected with each other via an optical fiber F143.

The period difference adjustment unit 32a receives and delays the probe light pulse, and feeds the delayed probe light pulse to the trigger signal output unit 60.

The period difference adjustment unit 32b receives and delays the output from the second photoelectric conversion unit 34b, and feeds the delayed output to the trigger signal output unit 60.

The fact that the period difference adjustment units 32a and 32b make the adjustment so that the value obtained by subtracting the period T3 from the period T4 is equal to the value obtained by subtracting a period T1 from the period T2 (for example, the adjustment so that the period T4 is equal to the period T2 and the period T3 is equal to the period T1, or the adjustment so that T4=T2=T3=T1) according to the variation of the third embodiment is the same as the period difference adjustment unit 32 according to the third embodiment.

The invention claimed is:
1. An optical measurement device, comprising:
a detected light pulse output device that receives a pump light pulse from a pump light source, and outputs detected light pulse having the same repetition frequency as the repetition frequency of the pump light pulse;
a signal output device that receives the detected light pulse and a probe light pulse from a probe light source, and outputs a signal corresponding to a power of the detected light pulse upon the reception of the probe light pulse;
a waveform measurer that measures a waveform of the output from the signal output device by detecting the output from the signal output device for a period from reception of a trigger signal to reception of a next trigger signal;
a first photoelectric converter that applies photoelectric conversion to the probe light pulse;
a second photoelectric converter that applies photoelectric conversion to the pump light pulse;
a first amplifier that amplifies an output from the first photoelectric converter;
a second amplifier that amplifies an output from the second photoelectric converter;
a trigger signal output device that outputs a cross-correlation of outputs of the first amplifier and the second amplifier as the trigger signal; and
a period difference adjuster that adjusts a difference in period between a period T3 from the output of the probe light pulse from the probe light source until the probe light pulse is fed, as the output from the first amplifier, to the trigger signal output device, and a period T4 from the output of the pump light pulse from the pump light source until the pump light pulse is fed, as the output from the second amplifier, to the trigger signal output device,
wherein the repetition frequency of the detected light pulse and the repetition frequency of the probe light pulse are different from each other.

2. The optical measurement device according to claim 1, wherein the trigger signal output device comprises:
an electric modulator that modulates the output from the first amplifier according to the output from the second amplifier;
an amplification device that amplifies an output from the electric modulator; and
a detector that detects an output from the amplification device according to the envelope detection.

3. The optical measurement device according to claim 1, wherein:
a period from the output of the probe light pulse from the probe light source until the probe light pulse is fed to the signal output device is T1;
a period from the output of the pump light pulse from the pump light source until the detected light pulse generated from the output pump light pulse is fed to the signal output device is T2; and
the period difference adjuster adjusts the period difference so that a value obtained by subtracting the period T3 from the period T4 is equal to a value obtained by subtracting the period T1 from the period T2.

4. The optical measurement device according to claim 3, wherein the period difference adjuster makes an adjustment such that the period T4 is equal to the period T2, and the period T3 is equal to the period T1.

5. The optical measurement device according to claim 4, wherein the period difference adjuster causes the periods T4, T2, T3 and T1 to be equal to each other.

6. The optical measurement device according to claim 1, wherein:
the pump light source and the detected light pulse output device are connected with each other via an optical fiber;
the probe light source and the signal output device are connected with each other via an optical fiber;
the probe light source and the first photoelectric converter are connected with each other via an optical fiber; and
the pump light source and the second photoelectric converter are connected with each other via an optical fiber.

7. An optical measurement device, comprising:
a detected light pulse output device that receives a pump light pulse from a pump light source, and outputs detected light pulse having the same repetition frequency as the repetition frequency of the pump light pulse;
a signal output device that receives the detected light pulse and a probe light pulse from a probe light source, and outputs a signal corresponding to a power of the detected light pulse upon the reception of the probe light pulse;
a waveform measurer that measures a waveform of the output from the signal output device by detecting the output from the signal output device for a period from reception of a trigger signal to reception of a next trigger signal;
a first photoelectric converter that applies photoelectric conversion to the probe light pulse;
a first amplifier that amplifies an output from the first photoelectric converter;
a trigger signal output device that outputs a cross-correlation of the output of the first amplifier and the pump light pulse as the trigger signal; and
a period difference adjuster that adjusts a difference in period between a period T3 from the output of the probe light pulse from the probe light source until the probe light pulse is fed, as the output from the first amplifier, to the trigger signal output device, and a period T4 from the output of the pump light pulse from the pump light source until the pump light pulse is fed to the trigger signal output device,
wherein the repetition frequency of the detected light pulse and the repetition frequency of the probe light pulse are different from each other.

8. The optical measurement device according to claim 7, wherein the trigger signal output device comprises:
a light modulator that modulates the pump light pulse according to the output from the first amplifier;
a photoelectric converter that applies photoelectric conversion to the output from the light converter;
an amplifier that amplifies an output from the photoelectric converter; and
a detector that detects an output from the amplification device according to the envelope detection.

9. The optical measurement device according to claim 7, wherein:
a period from the output of the probe light pulse from the probe light source until the probe light pulse is fed to the signal output device is T1;
a period from the output of the pump light pulse from the pump light source until the detected light pulse generated from the output pump light pulse is fed to the signal output device is T2; and
the period difference adjuster adjusts the period difference so that a value obtained by subtracting the period T3 from the period T4 is equal to a value obtained by subtracting the period T1 from the period T2.

10. The optical measurement device according to claim 9, wherein the period difference adjuster makes an adjustment such that the period T4 is equal to the period T2, and the period T3 is equal to the period T1.

11. The optical measurement device according to claim 10, wherein the period difference adjuster causes the periods T4, T2, T3 and T1 to be equal to each other.

12. The optical measurement device according to claim 7, wherein:
the pump light source and the detected light pulse output device are connected with each other via an optical fiber;

the probe light source and the signal output device are connected with each other via an optical fiber;

the probe light source and the first photoelectric converter are connected with each other via an optical fiber; and the pump light source and the trigger signal output device are connected with each other via an optical fiber.

13. An optical measurement device, comprising:

a detected light pulse output device that receives a pump light pulse from a pump light source, and outputs detected light pulse having the same repetition frequency as the repetition frequency of the pump light pulse;

a signal output device that receives the detected light pulse and a probe light pulse from a probe light source, and outputs a signal corresponding to a power of the detected light pulse upon the reception of the probe light pulse;

a waveform measurer that measures a waveform of the output from the signal output device by detecting the output from the signal output device for a period from reception of a trigger signal to reception of a next trigger signal;

a photoelectric converter that applies photoelectric conversion to the pump light pulse;

an amplifier that amplifies an output from the photoelectric converter;

a trigger signal output device that outputs a cross-correlation of the probe light pulse and the output of the amplifier as the trigger signal; and a period difference adjuster that adjusts a difference in period between a period T3 from the output of the probe light pulse from the probe light source until the probe light pulse is fed to the trigger signal output device, and a period T4 from the output of the pump light pulse from the pump light source until the pump light pulse is fed, as the output from the amplifier, to the trigger signal output device, wherein the repetition frequency of the detected light pulse and the repetition frequency of the probe light pulse are different from each other.

14. The optical measurement device according to claim 13, wherein the trigger signal output device comprises:

a light modulator that modulates the probe light pulse according to the output from the amplifier;

a photoelectric converter that applies photoelectric conversion to the output from the light modulator;

an amplification device that amplifies an output from the photoelectric converter; and a detector that detects an output from the amplification device according to the envelope detection.

15. The optical measurement device according to claim 13, wherein:

a period from the output of the probe light pulse from the probe light source until the probe light pulse is fed to the signal output device is T1;

a period from the output of the pump light pulse from the pump light source until the detected light pulse generated from the output pump light pulse is fed to the signal output device is T2; and the period difference adjuster adjusts the period difference so that a value obtained by subtracting the period T3 from the period T4 is equal to a value obtained by subtracting the period T1 from the period T2.

16. The optical measurement device according to claim 15, wherein the period difference adjuster makes an adjustment such that the period T4 is equal to the period T2, and the period T3 is equal to the period T1.

17. The optical measurement device according to claim 16, wherein the period difference adjuster causes the periods T4, T2, T3 and T1 are equal to each other.

18. The optical measurement device according to claim 13, wherein:

the pump light source and the detected light pulse output device are connected with each other via an optical fiber;

the probe light source and the signal output device are connected with each other via an optical fiber;

the probe light source and the trigger signal output device are connected with each other via an optical fiber; and the pump light source and the second photoelectric converter are connected with each other via an optical fiber.

19. A trigger signal generation device comprising:

a first photoelectric converter that applies photoelectric conversion to the probe light pulse;

a second photoelectric converter that applies photoelectric conversion to the pump light pulse;

a first amplifier that amplifies an output from the first photoelectric converter;

a second amplifier that amplifies an output from the second photoelectric converter;

a trigger signal output device that outputs a cross-correlation of outputs of the first amplifier and the second amplifier as the trigger signal; and a period difference adjuster that adjusts a difference in period between a period T3 from the output of the probe light pulse from the probe light source until the probe light pulse is fed, as the output from the first amplifier, to the trigger signal output device, and a period T4 from the output of the pump light pulse from the pump light source until the pump light pulse is fed, as the output from the second amplifier, to the trigger signal output device, wherein the repetition frequency of the pump light pulse and the repetition frequency of the probe light pulse are different from each other.

20. The trigger signal generation device according to claim 19, wherein the trigger signal output device comprises:

an electric modulator that modulates the output from the first amplifier according to the output from the second amplifier;

an amplification device that amplifies an output from the electric modulator; and a detector that detects an output from the amplification device according to the envelope detection.

21. The trigger signal generation device according to claim 19, wherein:

the probe light source and the first photoelectric conversion unit are connected with each other via an optical fiber; and the pump light source and the second photoelectric converter are connected with each other via an optical fiber.

22. A trigger signal generation device, comprising:

a first photoelectric converter that applies photoelectric conversion to the probe light pulse;

a first amplifier that amplifies an output from the first photoelectric converter;

a trigger signal output device that outputs a cross-correlation of the output of the first amplifier and the pump light pulse as the trigger signal; and a period difference adjuster that adjusts a difference in period between a period T3 from the output of the probe light pulse from the probe light source until the probe light pulse is fed, as the output from the first amplifier, to the trigger signal output device, and a period T4 from the output of the pump light pulse from the pump light source until the pump light pulse is fed to the trigger signal output device,
wherein the repetition frequency of the pump light pulse and the repetition frequency of the probe light pulse are different from each other.

23. The trigger signal generation device according to claim 22,
wherein the trigger signal output device comprises:
a light modulator that modulates the pump light pulse according to the output from the first amplifier;
a photoelectric converter that applies photoelectric conversion to the output from the light modulator;
an amplification device that amplifies an output from the photoelectric converter; and
a detector that detects an output from the amplification device according to the envelope detection.

24. The trigger signal generation device according to claim 22, wherein:
the probe light source and the first photoelectric converter are connected with each other via an optical fiber; and
the pump light source and the trigger signal output device are connected with each other via an optical fiber.

25. A trigger signal generation device, comprising:
a photoelectric converter that applies photoelectric conversion to a pump light pulse;
an amplifier that amplifies an output from the photoelectric converter;
a trigger signal output device that outputs a cross-correlation of a probe light pulse and the output of the amplifier as the trigger signal; and
a period difference adjuster that adjusts a difference in period between a period T3 from the output of the probe light pulse from the probe light source until the probe light pulse is fed to the trigger signal output device, and a period T4 from the output of the pump light pulse from the pump light source until the pump light pulse is fed, as the output from the amplifier, to the trigger signal output device,
wherein the repetition frequency of the pump light pulse and the repetition frequency of the probe light pulse are different from each other.

26. The trigger signal generation device according to claim 25,
wherein the trigger signal output device comprises:
a light modulator that modulates the probe light pulse according to the output from the amplifier;
a photoelectric converter that applies photoelectric conversion to the output from the light modulator;
an amplification device that amplifies an output from the photoelectric converter; and
a detector that detects an output from the amplification device according to the envelope detection.

27. The trigger signal generation device according to claim 25, wherein:
the probe light source and the trigger signal output device are connected with each other via an optical fiber; and
the pump light source and the photoelectric converter are connected with each other via an optical fiber.

* * * * *